(12) United States Patent
Smith (10) Patent No.: US 7,887,514 B2
(45) Date of Patent: *Feb. 15, 2011

(54) PNEUMOPERITONEUM NEEDLE

(75) Inventor: Robert C. Smith, Middletown, CT (US)

(73) Assignee: Tyco Healthcare Group LP, North Haven, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 12/616,329

(22) Filed: Nov. 11, 2009

(65) Prior Publication Data

US 2010/0056987 A1 Mar. 4, 2010

Related U.S. Application Data

(60) Continuation of application No. 11/475,422, filed on Jun. 26, 2006, now Pat. No. 7,618,399, which is a division of application No. 10/770,980, filed on Feb. 3, 2004, now abandoned.

(51) Int. Cl.
 *A61M 5/178* (2006.01)

(52) U.S. Cl. ............... 604/167.03; 604/164.01; 604/164.02; 604/164.08; 604/164.12; 604/246; 604/249

(58) Field of Classification Search ............ 604/23, 604/24, 25, 26
See application file for complete search history.

(56) References Cited

U.S. PATENT DOCUMENTS

| | | | |
|---|---|---|---|
| 2,623,521 A | 12/1952 | Shaw | |
| 4,180,068 A | 12/1979 | Hansen et al. | |
| 4,808,168 A | 2/1989 | Warring | |
| 4,869,717 A | 9/1989 | Adair | |
| 5,098,388 A | 3/1992 | Kulkashi et al. | |
| 5,104,381 A | 4/1992 | Gresl et al. | |
| 5,137,509 A | 8/1992 | Freitas | |
| 5,256,148 A | 10/1993 | Smith et al. | |
| 5,300,084 A | 4/1994 | Johnson | |
| 5,312,351 A | 5/1994 | Gerrone | |
| 5,352,206 A | 10/1994 | Cushieri et al. | |
| 5,374,252 A | 12/1994 | Banks et al. | |
| 5,374,253 A | 12/1994 | Burns et al. | |
| 5,423,760 A | 6/1995 | Yoon et al. | |
| 5,454,791 A | 10/1995 | Tovey et al. | |
| 5,470,316 A | 11/1995 | Tovey et al. | |
| 5,562,611 A | 10/1996 | Transue | |
| 5,665,072 A | 9/1997 | Yoon | |
| 5,743,881 A | 4/1998 | Demco | |
| 6,193,692 B1 | 2/2001 | Harris et al. | |
| 6,299,592 B1 | 10/2001 | Zander | |

(Continued)

FOREIGN PATENT DOCUMENTS

EP 0512462 A 11/1992

(Continued)

*Primary Examiner*—Kevin C Sirmons
*Assistant Examiner*—Laura C Schell (57) ABSTRACT

Pneumoperitoneum needles for providing and/or insufflating a corporal and/or abdominal cavity are provided. The pneumoperitoneum needle can include a housing, an elongate tubular body extending from a distal surface of the housing, and an elongate hollow tubular rod slidably received within the tubular body. The tubular body preferably includes a passage formed therethrough for connection to a gas administration system. The tubular rod preferably includes a blunt distal end defining an opening, and a proximal end portion defining an opening formed therethrough.

20 Claims, 5 Drawing Sheets

U.S. PATENT DOCUMENTS

| | | |
|---|---|---|
| 6,478,775 B1 | 11/2002 | Galt et al. |
| 7,329,233 B2 | 2/2008 | Gresham |
| 2004/0230160 A1 | 11/2004 | Bianco |

FOREIGN PATENT DOCUMENTS

| | | |
|---|---|---|
| FR | 902521 | 9/1945 |
| FR | 2727848 A1 | 9/1994 |
| JP | 09140721 A | 6/1997 |

PNEUMOPERITONEUM NEEDLE

CROSS-REFERENCE TO RELATED APPLICATION

The present application is a Continuation Application which claims the benefit of and priority to U.S. application Ser. No. 11/475,422, filed on Jun. 26, 2006, now U.S. Pat. No. 7,618,399 which is a Divisional Application claiming the benefit of and priority to U.S. application Ser. No. 10/770,980, filed Feb. 3, 2004, now abandoned the entire content of each of which being incorporated herein by reference.

BACKGROUND

1. Technical Field

The present disclosure relates to needles and, more particularly, to pneumoperitoneum needles for introducing gaseous fluids into a peritoneal cavity for inflating the peritoneal cavity prior to laparoscopic surgery.

2. Background of Related Art

Laparoscopic and endoscopic surgery has been widely accepted as the preferred surgical procedure for treatment of a variety of disorders that were formally treated with conventional surgical techniques.

In laparoscopic procedures, surgery is performed in the interior of the abdomen (e.g., the peritoneal cavity) through a small incision extending through the peritoneal cavity wall; in endoscopic procedures, surgery is performed in any hollow viscus of the body through narrow endoscopic tubes inserted through small entrance wounds in the skin.

In conjunction with laparoscopic surgery, pneumoperitoneum gases are generally introduced into the peritoneal cavity to expand the peritoneal cavity and raise the peritoneal cavity wall away from the vital organs therein. Thereafter, a trocar (e.g., a sharp pointed instrument) is inserted into a cannula assembly and used to puncture the inner lining of the peritoneal cavity. The trocar is then withdrawn and a laparoscopic surgical instrument is inserted through the cannula assembly to perform the desired surgery.

A conventional system used for introducing the pneumoperitoneum gases into the peritoneal cavity includes a pneumoperitoneum needle connected to a gas source via a flexible conduit. The pneumoperitoneum needle typically employed is a Veress-type needle which includes an elongated hollow outer sheath with a sharpened distal end for penetrating the inner lining of the peritoneal cavity. A spring-loaded blunt stylet is axially movable within the sheath and is distally biased so that the blunt end of the stylet retracts as the needle penetrates the inner lining and then advances to extend beyond the sharp end of the needle once the needle penetrates the inner lining of the peritoneal cavity. The pneumoperitoneum gas administering system also typically includes at least one volume flow regulator to control the rate of gas flow through the needle. Examples of such systems used for introducing pneumoperitoneum gases are disclosed in U.S. Pat. No. 4,808,168 and U.S. Pat. No. 5,104,381, the entire contents of each of which are incorporated herein by reference.

Typically, a surgeon observes the gas source to determine when the pneumoperitoneum needle has passed through the abdominal wall, into the peritoneal cavity, and the flow of gas commences.

In view of the foregoing, a continuing need exists for improved pneumoperitoneum needles for introducing gaseous fluids into a peritoneal cavity for inflating the peritoneal cavity prior to laparoscopic surgery. In particular, an indication of gas flow and/or passage into the peritoneal cavity is desired.

SUMMARY

Pneumoperitoneum needles for providing and/or insufflating a corporal and/or abdominal cavity are provided. In accordance with an aspect of the present disclosure, the pneumoperitoneum needle may include a housing, an elongate tubular body extending from a distal surface of the housing, and an elongate hollow tubular rod slidably received within the tubular body. The tubular body preferably includes a radially oriented passage formed therethrough for connection to a gas administration system. The tubular rod preferably includes a blunt distal end defining at least one distal opening (e.g., distally oriented, radially oriented and/or angularly oriented), and a proximal end portion defining at least one proximal opening (e.g., distally oriented, radially oriented and/or angularly oriented) formed therein.

The tubular rod includes a first position in which the opening formed in the proximal end thereof is in registration with a passage formed in the tubular body. The tubular body also includes a second position in which the opening formed in the proximal end thereof is out of registration with the passage formed in the tubular body.

The needle according to the present embodiment desirably further includes at least a pair of seal members disposed between the tubular body and the tubular rod. A first of the pair of seal members can be disposed distal of the radially oriented passage and a second of the pair of seal members can be disposed proximal of the radially oriented passage. Each seal member is preferably an O-ring fabricated from an elastomeric material. Preferably, each seal member is fixedly positioned relative to the tubular body.

Alternatively, it is envisioned that the tubular body may include an annular rib extending around the inner periphery thereof and/or the tubular rod can include an annular rib extending around the outer periphery thereof, thereby reducing the gap distance between the tubular rod and the tubular body to thereby reduce the passage of fluid therebetween. In addition, it is envisioned that a lubricant may be provided between the tubular body and the tubular rod to thereby inhibit the flow of fluid therebetween.

Alternatively, it is further envisioned that a close tolerance can be provided between the tubular body and the tubular rod such that passage of fluid between the tubular body and the tubular rod is inhibited.

It is envisioned that when the tubular rod is in the first position the opening formed in the proximal end thereof is positioned between the first and the second seal member. When the tubular rod is in the second position the radially oriented opening is positioned proximal of the second seal member.

Preferably, the tubular rod is biased to the first position. Accordingly, it is envisioned that the pneumoperitoneum needle may include a spring disposed between the housing and the tubular rod to bias the tubular rod to the first position.

The tubular body defines a cavity between the radially oriented opening formed in the proximal end thereof and the distally oriented opening formed in the blunt end thereof. The tubular body desirably includes a distal end defining a piercing tip. The tubular rod is dimensioned such that when the tubular rod is in the first position the distal end of the tubular rod extends beyond the piercing tip of the tubular body and when the tubular rod is in the second position the piercing tip of the tubular body extends beyond the distal end of the tubular rod.

The pneumoperitoneum needle according to the present embodiment may further include a gas administering system operatively connectable to the radially oriented passage formed in the tubular body. The gas administering system desirably delivers insufflation gases to the abdominal cavity. The gas administering system includes a source of insufflation gas, a conduit fluidly interconnecting the source of insufflation gas to the radially oriented passage formed in the tubular body, and a valve in fluid communication with the conduit for regulating the flow of insufflation gas through the conduit. The gas administering system can further include a gauge for measuring at least one of the volume, quantity and pressure of insufflation gas delivered to the abdominal cavity.

According to another aspect of the present disclosure, the pneumoperitoneum needle can include an elongate tubular body, an elongate hollow tubular rod slidably disposed within the tubular body, a valve assembly at a proximal end of the tubular body and including a manifold, and a stem mounted within the manifold. The manifold and the stem being movable with respect to one another so as to form a fluid path communicating with an indicator chamber in a first position, and a fluid path with the interior of the tubular rod, in a second position.

The pneumoperitoneum needle may include a first O-ring disposed between the manifold and the stem, the first O-ring being positioned distal of a passage communicating with the indicator chamber; and a second O-ring disposed between the manifold and the stem, the second O-ring being positioned proximal of the passage. Accordingly, when the tubular rod is in a first position, an opening formed in the manifold is positioned distal of the first O-ring, and when the tubular rod is in a second position, the opening formed in the manifold is positioned between the first O-ring and the second O-ring. Each of the first and second O-rings is fixedly positioned relative to the tubular body.

Preferably, the tubular rod is biased to the first position. The pneumoperitoneum needle may further include a spring member operatively positioned to bias the tubular rod to the first position.

The pneumoperitoneum needle may further include a housing for supporting the tubular body, the tubular body extending from a distal surface thereof. Desirably, the spring is disposed between a distally oriented surface of the stem and a proximally oriented surface of the tubular rod. The proximal portion of the tubular rod defines an enlarged portion and the spring is disposed in the enlarged portion.

The tubular body includes a distal end defining a piercing tip. The tubular rod is preferably dimensioned such that when the tubular rod is in the first position the distal end of the tubular rod extends beyond the piercing tip of the tubular body and when the tubular rod is in the second position the piercing tip of the tubular body extends beyond the distal end of the tubular rod.

The pneumoperitoneum needle may include a gas administering system operatively connectable to the opening formed in the manifold. The gas administering system being capable of delivering insufflation gases to the abdominal cavity. The gas administering system can include a source of insufflation gas; a conduit fluidly interconnecting the source of insufflation gas to a port in communication with the opening in the manifold; and a valve in fluid communication with the conduit for regulating the flow of insufflation gas through the conduit. The gas administering system may further include a gauge for measuring at least one of the volume, quantity and pressure of insufflation gas delivered to the abdominal cavity.

Additional advantages will become apparent from the description which follows, taken in conjunction with the accompanying drawings.

BRIEF DESCRIPTION OF THE DRAWINGS

The present disclosure will be further described with reference to the accompanying drawings, wherein like reference numerals refer to like parts in the several views, and wherein.

DETAILED DESCRIPTION OF PREFERRED EMBODIMENTS

Preferred embodiments of the presently disclosed pneumoperitoneum needles will now be described in detail with reference to the drawing figures wherein like reference numerals identify similar or identical elements. In the drawings and in the description which follows, the term "proximal", as is tradition, will refer to the end of the pneumoperitoneum needle of the present disclosure which is closest to the operator, while the term "distal" will refer to the end of the pneumoperitoneum needle which is furthest from the operator.

Figure 1:
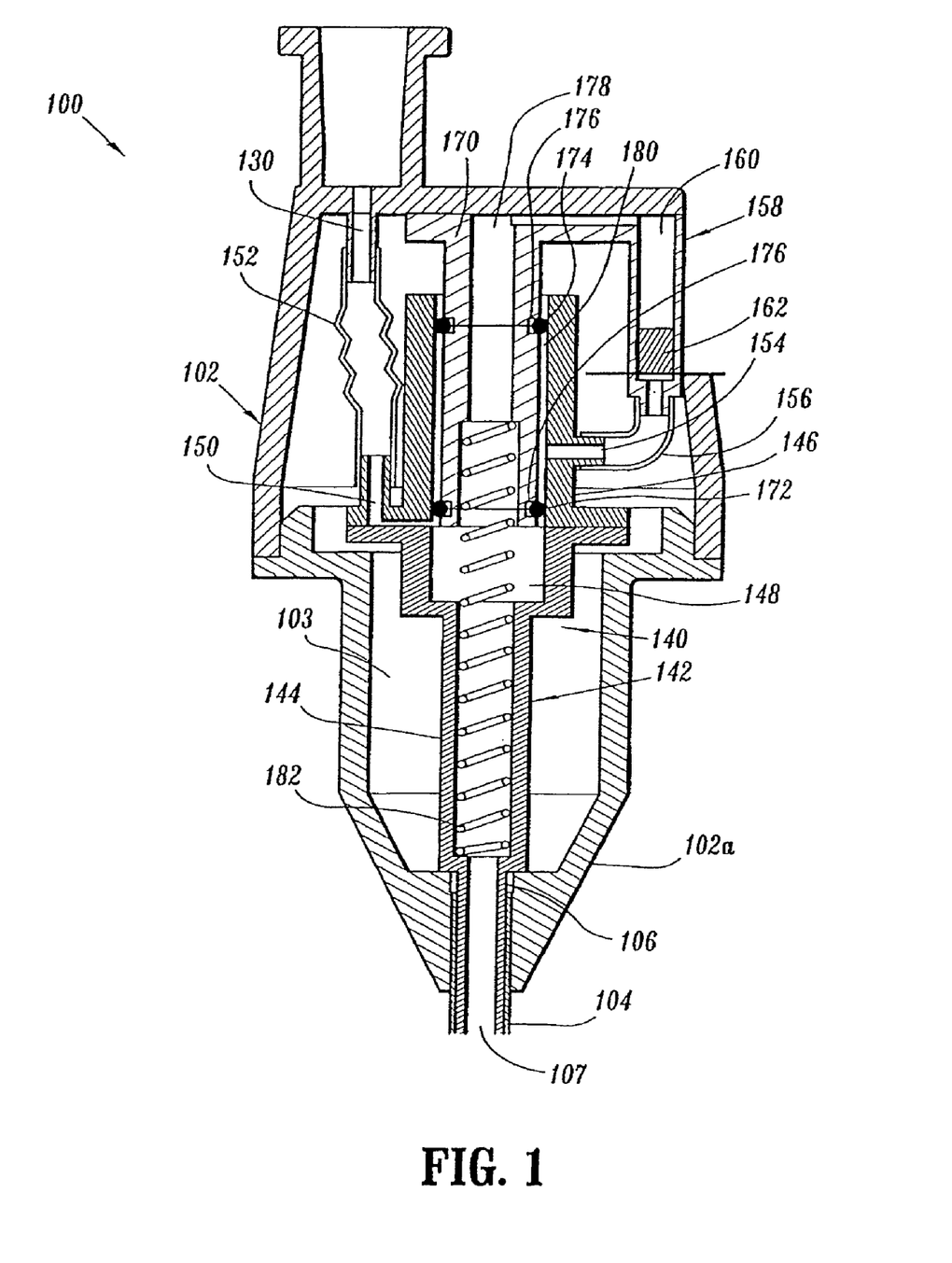
FIG. 1 is a longitudinal cross-sectional view of a pneumoperitoneum needle constructed in accordance with an embodiment of the present disclosure, while in a first position.
Figure 2:
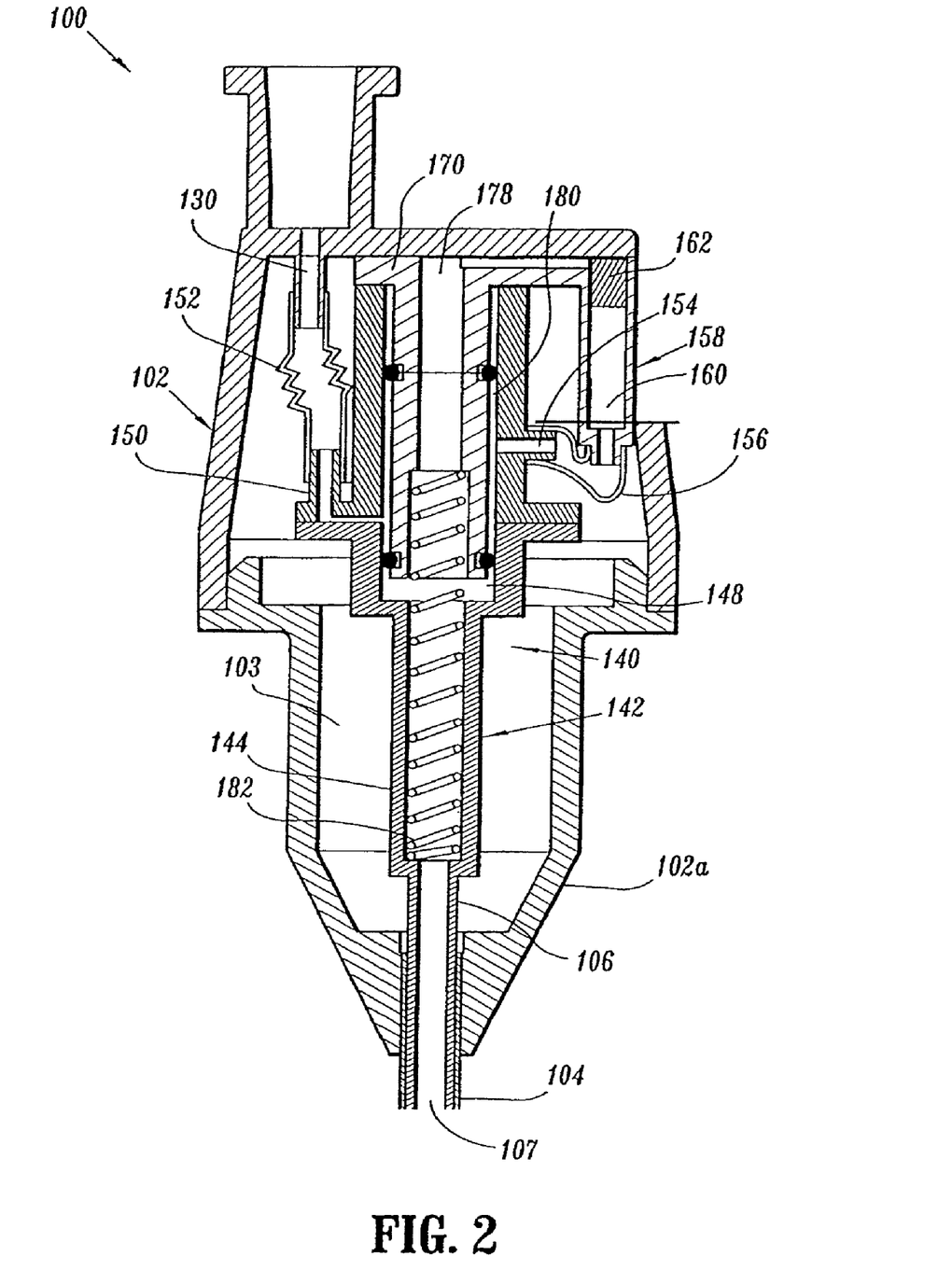
FIG. 2 is a longitudinal cross-sectional view of a pneumoperitoneum needle in accordance with the embodiment of FIG. 1, while in a second position.

With reference to FIGS. 1 and 2, a pneumoperitoneum needle, in accordance with an embodiment of the present disclosure, is shown generally as reference numeral 100. Needle 100 serves as a conduit between a source of pneumoperitoneum gas "A" (e.g., air, $CO_2$, etc) and the peritoneal cavity "C" (see FIGS. 5 and 6), wherein the pneumoperitoneum gas "A" may enter and expand peritoneal cavity "C" to provide improved access to the internal organs therewithin during laparoscopic surgery. While the embodiments of the following disclosure will relate primarily to laparoscopic surgery, it is envisioned and within the scope of the present disclosure to apply the principles disclosed herein to numerous other surgical procedures, including, and not limited to, endoscopic, arthroscopic, and the like.

Pneumoperitoneum needle 100 includes a handle or housing 102 defining a chamber 103 therein, an elongated hollow tubular body 104 operatively connected to a distal end 102a of housing 102, and a tubular rod 106, including a lumen 107 extending therethrough, slidably received within tubular body 104. Tubular body 104 has a distal end that is shaped for penetrating the lining of the pneumoperitoneum cavity. The distal tip of tubular body 106 is generally blunt and defines one or more openings. Pneumoperitoneum needle 100 is desirably operatively connected to, preferably in fluid engagement with, a pneumoperitoneum gas administering system or source of pneumoperitoneum gas (not shown). Housing 102 further includes a port 130 formed therein for fluid communication with the gas administering system. Although port 130 is shown as being longitudinally oriented, it is envisioned and within the scope of the present disclosure, that other orientations for port 130 are possible.

Pneumoperitoneum needle 100 further includes a valve assembly 140 operatively disposed within chamber 103 of housing 102. Valve assembly 140 includes a manifold 142 having a distal portion 144 and a proximal portion 146 operatively secured to one another. Manifold 142 has an inner surface 171 defining a lumen 148 through manifold 142. Tubular rod 106 is operatively connected to and extends distally from distal portion 144 of manifold 142 in a manner such that lumen 107 of tubular rod 106 is in fluid communication with lumen 148 of manifold 142.

Valve assembly 140 includes a first passage 150 formed in manifold 142 and in fluid communication with lumen 148. A conduit 152 inter-connects first passage 150 to port 130 of tubular body 104. Conduit 152 may comprise a passage, hose, tube of the like for fluidly connecting first passage 150 to port 130. Preferably, conduit 152 is fabricated from flexible tubing or the like.

Valve assembly 140 further includes a stem 170 extending distally from the inner surface of housing 102. Preferably, stem 170 is slidably received in proximal portion 146 of manifold 142. A distal seal member 172 and a proximal seal member 174 are provided and surround stem 170. Seal members 172, 174 create a fluid tight seal between the outer surface of stem 170 and the inner surface 171 of manifold 142 defining lumen 148. Seal members 172, 174 are preferably silicone-based O-type seals. Preferably, seal members 172, 174 are seated within annular grooves 176 formed in the outer surface of stem 170, or are otherwise attached to stem 170 or manifold 142. In this manner, seal members 172, 174 remain in position relative to stem 170 as manifold 142 is displaced axially therealong.

Stem 170 is sized to define an annular channel 180 between the outer surface thereof and the inner surface 171 of manifold 142. Seal members 172, 174 bound the upper end and the lower end of annular channel 180.

Valve assembly 140 includes an indictor 158 defining an indicator chamber 160 therein and having a float 162 operatively disposed therein. Preferably, indicator 158 is formed of a transparent material such that float 162 is visible by the operator.

Indicator 158 informs the user/operator of pneumoperitoneum needle 100 whether pneumoperitoneum gas "A" is flowing into peritoneal cavity "C" or not. In the embodiment shown in FIGS. 1 and 2, stem 170 defines a channel 178 therethrough which is in fluid communication with a proximal region 159 of indicator chamber 160. Accordingly, as will be described in greater detail below, when float 162 is in a distal region 161 of indicator chamber 160, as seen in FIG. 1, indicator 158 advises the user that pneumoperitoneum gas "A" is flowing into peritoneal cavity "C". Moreover, when float 162 is in a proximal region 159 of chamber 160, as seen in FIG. 2, indicator 158 advises the user that no pneumoperitoneum gas "A" is flowing into peritoneal cavity "C".

Valve assembly 140 further includes a second passage 154 extending through proximal portion 146 of manifold 142 and communicating with annular channel 180. A conduit 156 is provided for fluidly inter-connecting second passage 154 to a distal region of chamber 160. Conduit 156 may comprise a passage, hose, tube or the like for fluidly connecting second passage 154 and indicator chamber 160.

The housing, valve assembly, tubular body, tubular rod, and other parts may be formed from appropriate polymeric or metal materials. For example, the housing and valve assembly may be formed from poly carbonate, whereas the tubular body and tubular rod are desirably stainless steel.

Valve assembly 140 includes a biasing member 182 disposed between stem 170 and manifold 142. Preferably, biasing member 182 is in the form of a coil spring, however, other types of biasing members, contemplated by those skilled in the art, are understood to be included herein. Biasing member 182 is desirably mounted between a distally-facing surface of stem 170 and the distal portion 144 of manifold 142, as shown. Biasing member 182 tends to maintain manifold 142 of valve assembly 140 in a distal-most or first position, as seen in FIG. 1. In this position, as shown in FIG. 1, distal seal member 172 is positioned distally of first passage 150. Tubular rod 106 is also in a distal-most position so that blunt distal tip 206a thereof is exposed and/or otherwise extends distally from tubular body 104.

Valve assembly 140 of pneumoperitoneum needle 100 is initially in the first position in which fluid flow through the needle is permitted. First passage 150 is connected to lumen 148 of manifold 142 and channel 178 of stem 170. Lumen 148 communicates with lumen 107 of tubular rod 106. Channel 178 communicates with region 159 of indicator chamber 160 to urge float 162 toward the distal region of indicator chamber 160.

Valve assembly 140 can be urged from the first position to a second position in which first passage 150 is disposed proximally of distal seal 172, as shown in FIG. 2. In the second position, fluid flow through the needle is blocked. Valve assembly 140 is urged to the second position by overcoming the bias of biasing member 182 and displacing tubular rod 106 in a proximal direction relative to tubular body 104. When valve assembly 140 is in the second position, first passage 150 is in fluid communication with annular channel 180 and, in turn, in fluid communication with second passage 154.

During use of pneumoperitoneum needle 100, when tip 210 (see FIGS. 2-6 and 8) of tubular body 104 is being inserted peritoneal cavity "C" and thus being pressed against the skin of the patient, distal tip 106a of tubular rod 106 is urged into tubular body 104 and, in turn, valve assembly 140 is urged from the first position to the second position. When valve assembly 140 is in the second position, gas "A" from a gas administering system or source (not shown) enters housing 102 through port 130. Gas "A" then flows through conduit 152, through first passage 150 and into annular channel 180 of manifold 142. Gas "A" then continues through annular channel 180 and out second passage 154, through conduit 156 and into a distal region 161 of indicator chamber 160 to thereby urge and/or displace float 162 in a proximal direction. Positioning of float 162 in the proximal region of indicator chamber 160 indicates to the user that gas "A" is not flowing into peritoneal cavity "C".

Once tip 210 of tubular body 104 completely penetrates the abdominal wall of the patient and distal tip 106a of tubular rod 106 is no longer substantially obstructed, biasing member 182 urges valve assembly 140 from the second position to the first position. In the first position, gas flows through first passage 150 and lumen 148 to lumen 107 of tubular rod 106, to supply gas to peritoneal cavity "C". Gas also flows from first passage 150 to channel 178, which communicates with proximal region 159 to position float 162 in the distal region 161 of indicator chamber 160. In this position, float 162 indicates to the user that gas "A" is flowing into peritoneal cavity "C".

Figure 3:
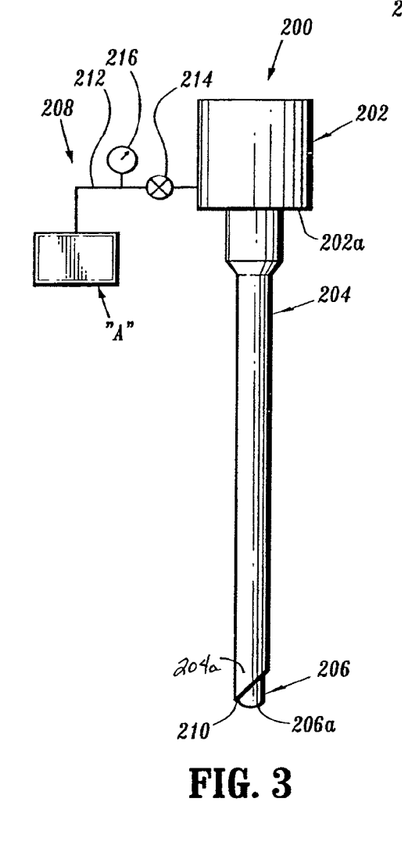
FIG. 3 is a side elevational view of a pneumoperitoneum needle constructed in accordance with another embodiment of the present disclosure.
Figure 4:
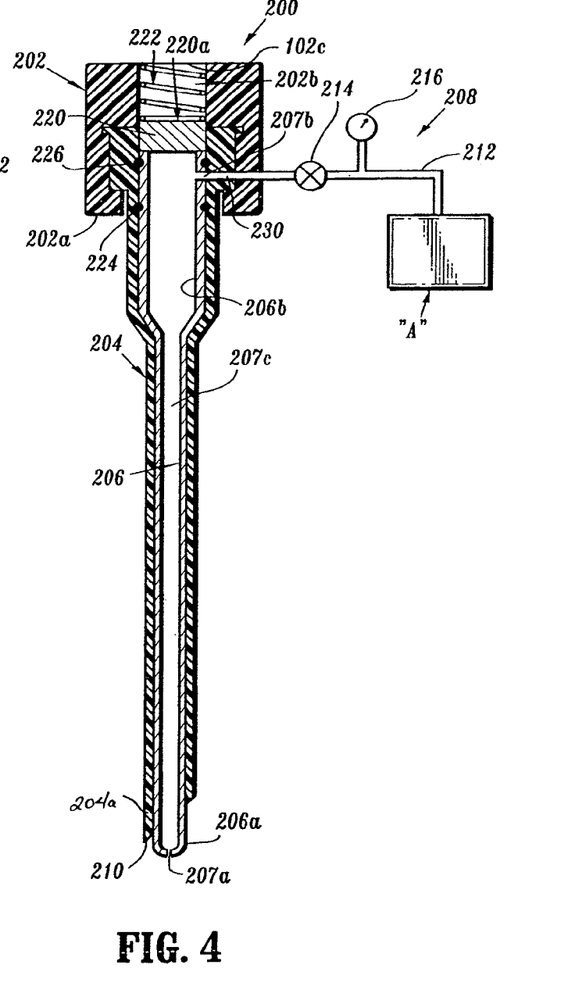
FIG. 4 is an enlarged longitudinal cross-sectional view of a pneumoperitoneum needle in accordance with the embodiment of FIG. 2.

Turning now to FIGS. 3-8, and in particular to FIGS. 3 and 4, a pneumoperitoneum needle in accordance with another embodiment of the present disclosure is shown generally as reference numeral 200.

Pneumoperitoneum needle 200 includes a handle or housing 202, an elongated hollow tubular body 204 operatively connected to a forward end 202a of housing 202, and a tubular rod 206 slidably received within tubular body 204. Pneumoperitoneum needle 200 is desirably operatively connected to, preferably in fluid engagement with a pneumoperitoneum gas administering system 208 or other source of gas. Tubular body 204 includes a piercing edge or tip 210 formed at a distal end 204a thereof for penetrating the inner lining of the peritoneal cavity. Tubular body 204 further includes a radially oriented passage 230 formed therein for fluid communication with gas administering system 208, as will be described in greater detail below. Although passage 230 is shown as being radially oriented, it is envisioned and within the scope of the present disclosure, that other orientations for passages 230 are possible. One skilled in the art would readily understand that passages 230 can be longitudinally oriented, angularly oriented, tangentially oriented and the like.

Figure 5:
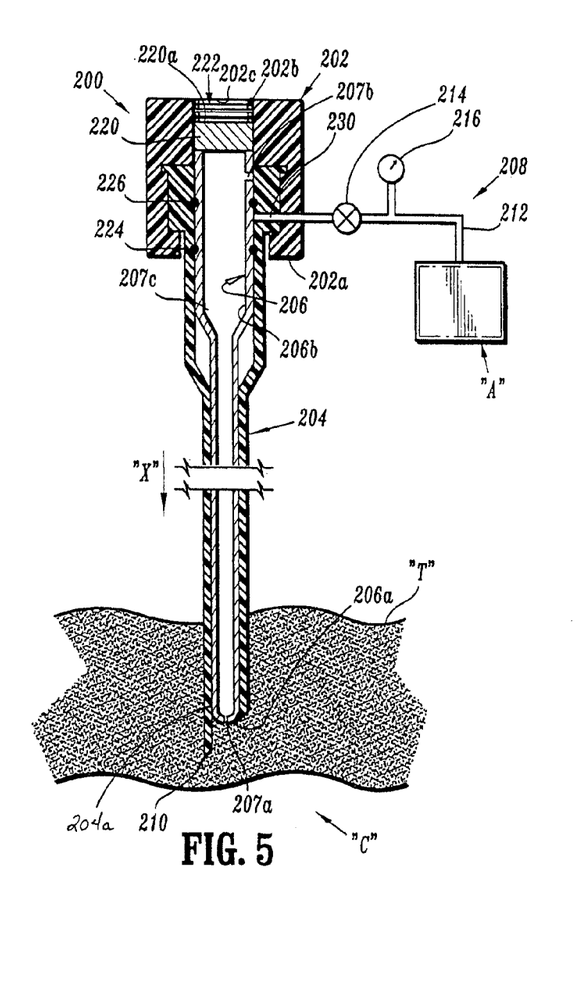
FIG. 5 is an enlarged longitudinal cross-sectional view of a pneumoperitoneum needle in accordance with the embodiment of FIGS. 3 and 4, illustrating a stage in the penetration of a distal end of the pneumoperitoneum needle through the abdominal wall.
Figure 6:
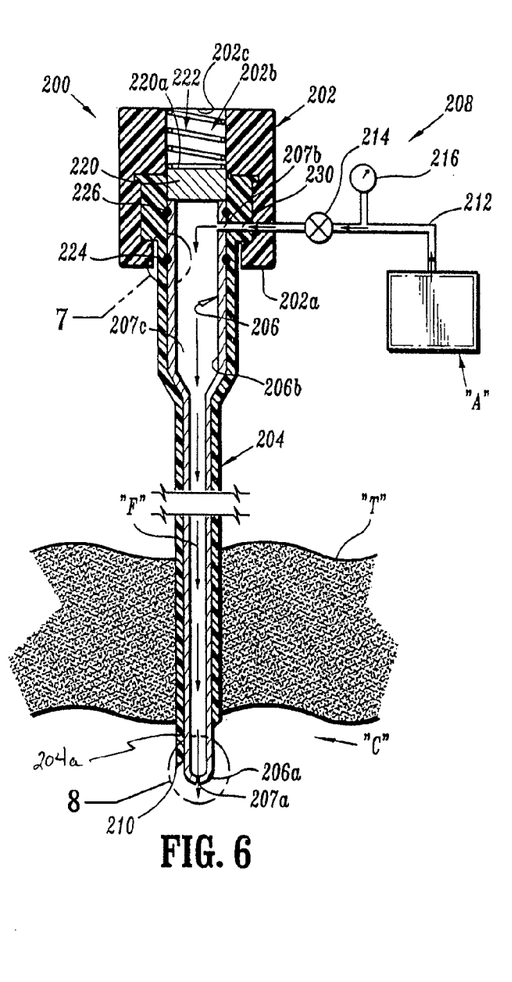
FIG. 6 is an enlarged longitudinal cross-sectional view of a pneumoperitoneum needle in accordance with the embodiment of FIGS. 3-5, illustrating a later stage in the penetration of the distal end of the pneumoperitoneum needle through the abdominal wall.

Tubular rod 206 includes a blunt distal tip 206a, a proximal end portion 206b receivable in a cavity 202b formed in housing 202, and defines an elongate, longitudinally extending cavity 207c therethrough. Distal tip 206a of tubular rod 206 defines an opening 207a formed therein, which is, in this embodiment, formed in a distally oriented direction, as seen in FIGS. 4-6. However, one or more openings may be provided in distal tip 206a, including openings in a radially-oriented direction. Although opening 207a is shown as being distally oriented, it is envisioned and within the scope of the present disclosure, that other orientations for opening 207a are possible. One skilled in the art would readily understand that openings 207a can be radially oriented, angularly oriented, tangentially oriented and the like.

Preferably, as seen in FIGS. 3-5, tubular rod 206 is sized such that distal tip 206a thereof extends beyond piercing edge 210 of tubular body 204 when tubular rod 206 is in a first or extended position. Tubular rod 206 further includes a radially oriented opening 207b formed in proximal end portion 206b thereof. Desirably, an end plate 220 is positioned against proximal end portion 206b in such a manner to close off proximal end portion 206b and to inhibit passage and/or escape of gases between end plate 220 and proximal end portion 206b of tubular rod 206. Alternatively, it is envisioned that tubular rod 206 can be manufactured having a closed or sealed proximal end portion 206b defined by a surface (not shown) which is substantially transversely oriented with respect to the longitudinal axis of pneumoperitoneum needle 200.

Tubular rod 206 is adapted to reciprocal longitudinal movement from a first or extended position, as shown in FIG. 6, to a second or retracted position, as shown in FIG. 5, and is biased to the first or extended position under the influence of a coil spring 222. Spring 222 is disposed within cavity 202b of housing 202 such that one end of spring 222 is in contact with a proximal surface 220a of end plate 220 and the opposite end of spring 222 is in contact with an inner distally oriented surface 202c of cavity 202b of housing 202.

Preferably, in use, when tubular rod 206 is in the first position, radially oriented opening 207b formed therein substantially aligns with and/or substantially comes into registration with radially oriented passage 230 of tubular body 204. Accordingly, as will be described in greater detail below, when tubular rod 206 is in the first position, pneumoperitoneum gas is allowed to enter cavity 207c. In addition, when tubular rod 206 is in the second position, radially oriented opening 207b formed therein is out of alignment and/or out of registration with radially oriented passage 230 of tubular body 204. Accordingly, as will be described in greater detail below, when tubular rod 206 is in the second position, pneumoperitoneum gas is prevented from entering cavity 207c.

Preferably, housing 202 and/or tubular rod 206 can be fabricated from a polymeric material such as an acrylic, polystyrene, polycarbonate and styrene-acrylonitrile (SAN) copolymer. In a preferred embodiment, housing 202 is molded as a single unit. Tubular body 204 is preferably fabricated from a hardened biocompatible material such as stainless steel or titanium.

Figure 7:
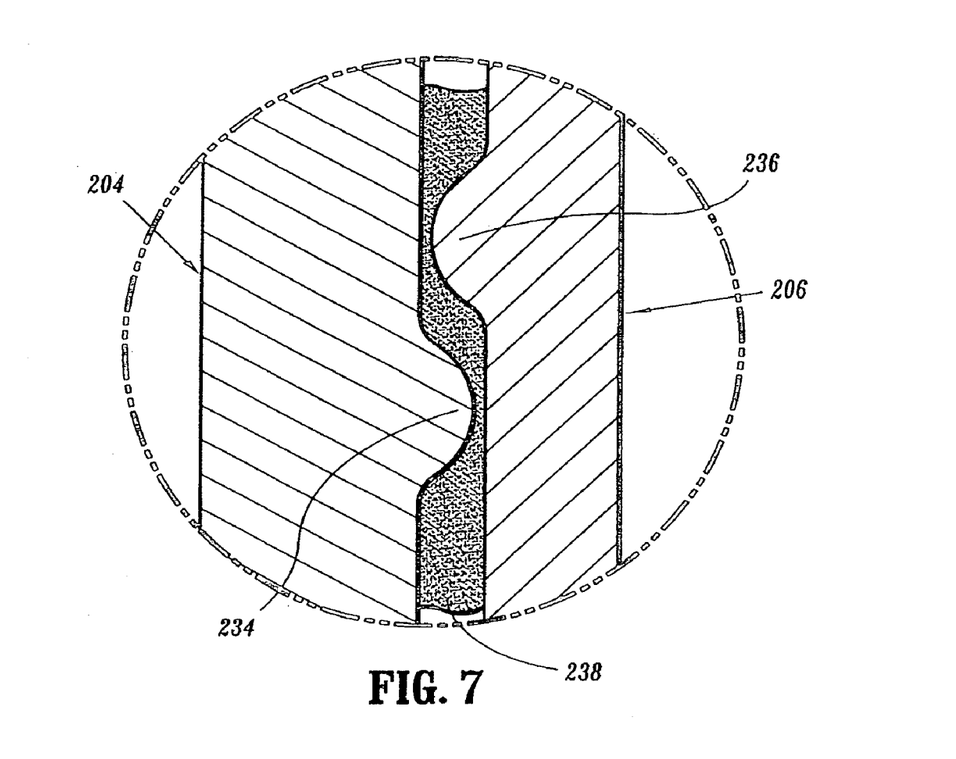
FIG. 7 is an enlarged view of the area indicated as 7 of FIG. 6.
Figure 8:
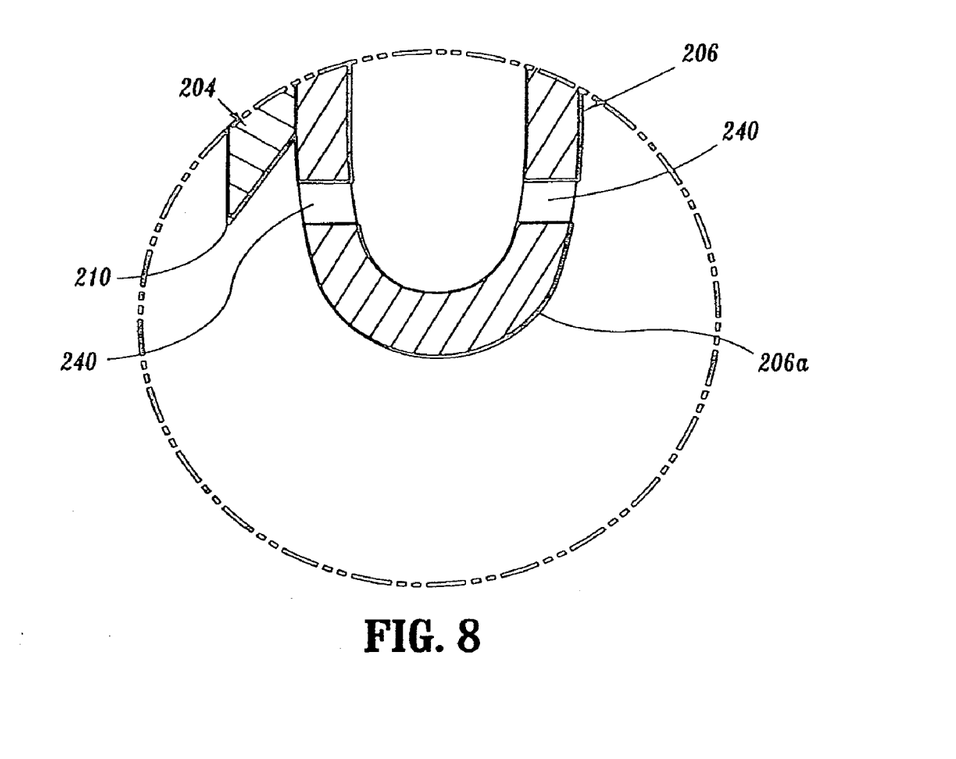
FIG. 8 is an enlarged view of the area indicated as 8 of FIG. 6.

As best seen in FIGS. 6-8, pneumoperitoneum needle 200 further includes a plurality of seals, preferably at least a pair of seals 224, 226 disposed between tubular body 204 and tubular rod 206. Seals 224, 226 are preferably O-ring type seals or gaskets and preferably completely surround the perimeter and/or periphery of tubular rod 206. Seals 224, 226 are preferably fabricated from a resilient elastomeric material, such as, for example, a rubber based material, a silicone based material, or the like. Seals 224, 226 are of the type which inhibit and/or otherwise prevent passage of gases along and through the space between tubular body 204 and tubular rod 206.

Desirably, seals 224, 226 are secured to the inner surface of tubular body 204 in such a manner such that when tubular rod 206 is axially displaced relative to tubular body 204, seals 224, 226 remain in position relative to tubular body 204 and allow tubular rod 206 to slide thereacross. Preferably, a bonding agent, adhesive or the like can be used to fixedly secure seals 224, 226 to the inner surface of tubular body 204. Alternatively, it is envisioned that the inner surface of tubular body 204 is provided with annular grooves (not shown), configured and/or otherwise dimensioned to receive a respective seal 224, 226 therein. In this manner, the annular grooves inhibit movement of seals 224, 226 relative to tubular body 204.

Preferably, as will be described in greater detail below, one of seals 224, 226 is disposed distal of radially oriented passage 230 of tubular body 204 while the other of seals 224, 226 is disposed proximally of radially oriented passage 230 of tubular body 204. In addition, seals 224, 226 are positioned such that when tubular rod 206 is in the first position, radially oriented opening 207b formed therein is positioned between seals 224, 226 (see FIG. 5) and is substantially aligned with radially oriented passage 230 of tubular body 204, as described above. Moreover, seals 224, 226 are positioned such that when tubular rod 206 is in the second position, radially oriented opening 207b formed therein is positioned proximal of the proximal-most seal 224, 226. While in the second position, proximal-most seal 224, 226 inhibits and/or otherwise prevents passage of pneumoperitoneum gas from radially oriented passage 230 of tubular body 204, through radially oriented opening 207b of tubular rod 206 and into cavity 207c of tubular rod 206.

While O-ring type seals 224, 226 are preferred, as seen in FIG. 7, it is envisioned that seals 224, 226 can include an annular rib 234 extending around the inner periphery of tubular body 204 and/or seals 224, 226 can include an annular rib 236 extending around the outer periphery of tubular rod 206, thereby reducing the gap distance between tubular rod 206 and tubular body 204 to thereby inhibit the passage of fluid therebetween. In addition, it is envisioned that a lubricant, such as a silicone based substance 238 (e.g., grease, gel or the like) can be provided between tubular body 204 and tubular rod 206 to thereby inhibit the flow of fluid therebetween.

Alternatively, it is envisioned that a close tolerance can be provided between tubular body 204 and tubular rod 206 such that passage of fluid between tubular body 204 and tubular rod 206 is inhibited.

Gas administering system 208 regulates the amount of insufflation gases, e.g., pneumoperitoneum gases, flowing through tubular body 204 and into the peritoneal cavity. Gas administering system 208 may be any conventional system suitable for this purpose. Gas administering system 208 preferably includes a source of insufflation gas "A", e.g., pneumoperitoneum gas, a conduit 212 fluidly interconnecting the source of gas "A" to pneumoperitoneum needle 200 to carry the insufflation gas to the needle destination, and a valve 214 (e.g., a stop-cock valve or the like) operatively associated (e.g., in fluid communication) with conduit 212 for regulating the flow of gas through conduit 212. Desirably, gas administering system 206 includes a gauge or indicator 216 operatively associated (i.e., in fluid communication) with conduit 212 for measuring the volume, quantity and/or pressure of gas delivered to peritoneal cavity "C".

With particular reference to FIGS. 5 and 6, a method of using pneumoperitoneum needle 200 will now be described. In use, as seen in FIG. 5, pneumoperitoneum needle 200 is placed against the surface of the patient's abdominal area "T" such that blunt distal tip 206a of tubular rod 206 contacts the surface of abdominal area "T". With distal tip 206a initially engaging and/or contacting the surface of abdominal area "T", distal force, as indicated by arrow "X", is applied to pneumoperitoneum needle 200. Pressing and/or advancing pneumoperitoneum needle 200 distally toward the surface of abdominal area "T", in the direction of arrow "X", results in tubular rod 206 being forced from the first position to the second position, thereby compressing spring 222 and placing piercing edge 210 of tubular body 204 in contact with the surface of abdominal area "T". When in the second position, flow of pneumoperitoneum gas, through cavity 207c and out distally oriented opening 207a, is at least substantially, preferably completely, stopped.

Continual distal force is applied to pneumoperitoneum needle 200 so that piercing edge 210 penetrates the surface of abdominal area "T" and enters abdominal cavity "C". As seen in FIG. 6, once piercing edge 210 enters abdominal cavity "C", tubular rod 206 moves distally, to its first position, under the influence of spring 222. In this position, radially oriented opening 207b of tubular rod 206 is brought into substantial alignment and/or registration with radially oriented passage 230 of tubular body 204.

Conduit 212 can then be connected to passage 230 of tubular body 204 and valve 214 opened to permit the pneumoperitoneum gas to flow (as shown by arrows "F") out from the source of gas "A", through conduit 212, through passage 230, through opening 207b, through cavity 207c, through opening 207a formed in distal tip 106a of tubular rod 206, and into abdominal cavity "C".

Abdominal cavity "C" is insufflated with pneumoperitoneum gas until gauge 216 reaches a particular predetermined level. Preferably, pneumoperitoneum gas is introduced at a sufficient volume and pressure to distend abdominal cavity "C" to a considerable extent. Once abdominal cavity "C" has been distended by a desired and/or a sufficient amount, valve 214 is closed until additional pneumoperitoneum gas is needed to re-distend abdominal cavity "C", or in the alternative, valve 214 is tightened to thereby reduce the rate of introduction of pneumoperitoneum gas into abdominal cavity "C" and thereby maintain abdominal cavity "C" at a uniform distended condition. It should be apparent that valve 214 can be adjusted as needed throughout the surgical procedure to insufflate and/or deflate abdominal cavity "C".

Although pneumoperitoneum needles 200 has been described in terms of specified embodiments which are set forth in detail above, it should be understood that this is by illustration only and that pneumoperitoneum needle 200 is not necessarily limited to the embodiments disclosed herein, since alternative embodiments and operating techniques will become apparent to those skilled in he art in view of the disclosure.

Accordingly, modifications are contemplated which can be made without departing from the spirit of the described pneumoperitoneum needle. For example, as seen in FIGS. 4-6, it is envisioned that proximal end portion 206b of tubular rod 206 is flared as compared to distal tip 206a (i.e., has a larger diameter as compared to the diameter of a distal portion thereof). In addition, tubular body 204 can include a flared proximal end portion 204b to accommodate flared proximal end portion 206b of tubular rod 206. As such, in use, flared proximal end portion 206b of tubular rod 206 abuts against the non-flared distal end portion 204a of tubular body 204, when tubular rod 206 is in the first position, thereby effectively limiting the distal advancement of tubular rod 206 relative to tubular body 204. In other embodiments, the tubular rod and/or the tubular body have a constant diameter, or other shape.

It is further envisioned that the outer surface of tubular rod 206 can include a element or member configured and adapted to engage and/or mate with a complementary member provided on the inner surface of tubular body 204 such that tubular rod 206 is inhibited and/or otherwise prevented from rotating about the longitudinal axis that thereby placing opening 207b of tubular rod 206 out of radial registration with passage 230 of tubular body 204.

While opening 207a formed in distal tip 206a is desirably distally oriented, as seen in FIG. 4, it is envisioned and within the scope of the present disclosure that opening 207a can be replaced with at least one radially oriented opening 240 formed in distal tip 206a of tubular rod 206, as shown in FIG. 8. It is further envisioned that tubular rod 206 can include both a distally oriented opening 207a and at least one radially oriented opening 240 (not shown). It is also envisioned that openings 240 can be oriented at an angle with respect to a longitudinal axis of tubular rod 206 (not shown).

While the above-disclosure relates primarily to a pneumoperitoneum needle configured to deliver an insufflation gas (e.g., pneumoperitoneum gas, $CO_2$ and the like) to the abdominal cavity, it is envisioned and within the scope of the present disclosure that the pneumoperitoneum needle can deliver any insufflation type fluid to the abdominal cavity, including and not limited to, saline, water, aqueous solutions and the like.

It is envisioned that various other modifications fall within the scope of the present disclosure without departing from the spirit of the same.

What is claimed is:

1. A pneumoperitoneum needle for insufflating a corporal cavity, the pneumoperitoneum needle comprising:
   an elongate tubular body;
   an elongate hollow tubular rod slidably disposed within the tubular body;
   a manifold connected to and in fluid communication with a proximal end of the tubular rod; and
   a tubular stem at least partially disposed within the manifold and in fluid communication therewith, the manifold being movable with respect to the stem between a first position and a second position upon a movement of the tubular rod relative to the tubular body, wherein the position of the manifold relative to the stem controls fluid flow through the elongate hollow tubular rod;
   wherein when the manifold is in the first position a fluid is communicated to the tubular rod, and when the manifold is in the second position said fluid is communicated to an indicator chamber to activate an indicator.

2. The pneumoperitoneum needle according to claim 1, further including:
   a first O-ring disposed between the manifold and the stem, the first O-ring being positioned distal of a passage communicating with the indicator chamber; and
   a second O-ring disposed between the manifold and the stem, the second O-ring being positioned proximal of the passage.

3. The pneumoperitoneum needle according to claim 2, wherein when the tubular rod is in a first position, an opening formed in the manifold is positioned distal of the first O-ring, and when the tubular rod is in a second position, the opening formed in the manifold is positioned between the first O-ring and the second O-ring.

4. The pneumoperitoneum needle according to claim 2, wherein each of the first and second O-rings is fixedly positioned relative to the stem.

5. The pneumoperitoneum needle according to claim 1, wherein the tubular rod is biased to the first position.

6. The pneumoperitoneum needle according to claim 1, further including a biasing member operatively positioned to bias the tubular rod to the first position.

7. The pneumoperitoneum needle according to claim 1, further comprising a housing for supporting the tubular body, wherein the tubular body extends distally from the housing.

8. The pneumoperitoneum needle according to claim 6, wherein the biasing member is disposed between a distally oriented surface of the stem and a proximally oriented surface of the tubular rod.

9. The pneumoperitoneum needle according to claim 1, wherein the tubular body includes a distal end defining a piercing tip.

10. The pneumoperitoneum needle according to claim 9, wherein the tubular rod is dimensioned such that when the tubular rod is in the first position the distal end of the tubular rod extends beyond the piercing tip of the tubular body and when the tubular rod is in the second position the piercing tip of the tubular body extends beyond the distal end of the tubular rod.

11. The pneumoperitoneum needle according to claim 3, further comprising a gas administering system operatively connectable to the opening formed in the manifold, wherein the gas administering system delivers insufflation gases to the operative site.

12. The pneumoperitoneum needle according to claim 11, wherein the gas administering system includes:
   a source of insufflation gas; and
   a conduit fluidly interconnecting the source of insufflation gas to a port in communication with the opening in the manifold.

13. The pneumoperitoneum needle according to claim 12, wherein the gas administering system further includes a gauge for measuring at least one of the volume, quantity and pressure of insufflation gas delivered to the operative site.

14. A pneumoperitoneum needle for insufflating a corporal cavity, the pneumoperitoneum needle comprising:
   an elongate tubular body;
   an elongate hollow tubular rod slidably disposed within the tubular body;
   a manifold connected to and in fluid communication with a proximal end of the tubular rod;
   a stem at least partially disposed within the manifold, the manifold being movable with respect to the stem between a first position and a second position upon a movement of the tubular rod relative to the tubular body, wherein the stem and the manifold are dimensioned to define an annular channel therebetween and wherein the position of the manifold relative to the stem controls fluid flow through the elongate hollow tubular rod; and
   an indicator chamber in fluid communication with the manifold and the stem, the indicator chamber including a floating indicator therein;
   wherein when the manifold is in the first position a fluid is communicated to the tubular rod, and when the manifold is in the second position said fluid is communicated to the indicator chamber to activate the indicator.

15. An insufflation system for insufflating a corporal cavity, the insufflation system comprising:
   a pneumoperitoneum needle configured to penetrate tissue and an deliver an insufflating fluid to the corporal cavity, the pneumoperitoneum needle comprising:
      an elongate tubular body;
      an elongate hollow tubular rod slidably disposed within the tubular body;
      a manifold connected to and in fluid communication with a proximal end of the tubular rod; and
      a tubular stem at least partially disposed within the manifold and in fluid communication therewith, the manifold being movable with respect to the stem between a first position and a second position upon a movement of the tubular rod relative to the tubular body, wherein the position of the manifold relative to the stem controls fluid flow through the elongate hollow tubular rod;
      wherein when the manifold is in the first position a fluid is communicated to the tubular rod, and when the manifold is in the second position said fluid is communicated to an indicator chamber to activate an indicator; and
   a gas administering system fluidly connected to the pneumoperitoneum needle, the gas administering system including:
      a source of insufflation gas; and
      a conduit fluidly interconnecting the source of insufflation gas to the manifold.

16. The insufflation system according to claim 15, wherein the pneumoperitoneum needle further includes:
   a first seal member disposed between the manifold and the stem, the first seal member being positioned distal of a passage communicating with the indicator chamber; and a second seal member disposed between the manifold and the stem, the second seal member being positioned proximal of the passage.

17. The insufflation system according to claim 16, wherein when the tubular rod of the pneumoperitoneum needle is in a first position, an opening formed in the manifold is positioned distal of the first seal member, and when the tubular rod is in a second position, the opening formed in the manifold is positioned between the first seal member and the second seal member.

18. The insufflation system according to claim 15, wherein the tubular rod of the pneumoperitoneum needle is biased to the first position.

19. The insufflation system according to claim 15, wherein the tubular rod of the pneumoperitoneum needle is dimensioned such that when the tubular rod is in the first position the distal end of the tubular rod extends beyond the piercing tip of the tubular body and when the tubular rod is in the second position the piercing tip of the tubular body extends beyond the distal end of the tubular rod.

20. The insufflation system according to claim 15, wherein the gas administering system further includes a gauge for measuring at least one of the volume, quantity and pressure of insufflation gas delivered to the operative site.

* * * * *